US007211557B2

(12) United States Patent
DiMarchi et al.

(10) Patent No.: US 7,211,557 B2
(45) Date of Patent: *May 1, 2007

(54) USE OF GLP-1 ANALOGS AND DERIVATIVES ADMINISTERED PERIPHERALLY IN REGULATION OF OBESITY

(75) Inventors: Richard DiMarchi, Carmel, IN (US); Suad Efendic, Lidingo (SE)

(73) Assignee: Eli Lilly and Company, Indianapolis, IN (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/429,522

(22) Filed: May 5, 2003

(65) Prior Publication Data

US 2004/0018975 A1  Jan. 29, 2004

Related U.S. Application Data

(63) Continuation of application No. 09/585,186, filed on Jun. 1, 2000, now Pat. No. 6,583,111, which is a continuation of application No. 08/961,405, filed on Oct. 30, 1997, now Pat. No. 6,191,102.

(60) Provisional application No. 60/030,213, filed on Nov. 5, 1996.

(51) Int. Cl.
*A01N 39/18* (2006.01)

(52) U.S. Cl. .............. 514/2; 514/12; 514/866; 514/909; 530/300; 530/308

(58) Field of Classification Search ............ None
See application file for complete search history.

(56) References Cited

U.S. PATENT DOCUMENTS

| 5,118,666 A | 6/1992 | Habener |
|---|---|---|
| 5,120,712 A | 6/1992 | Habener |
| 5,512,549 A | 4/1996 | Chen et al. |
| 5,545,618 A | 8/1996 | Buckley et al. |
| 5,693,609 A * | 12/1997 | Baker et al. ............ 514/3 |
| 5,762,953 A * | 6/1998 | Venkateshwaran ...... 424/448 |
| 6,191,102 B1 | 2/2001 | DiMarchi et al. |
| 6,583,111 B1 | 6/2003 | DiMarchi et al. |

FOREIGN PATENT DOCUMENTS

| EP | 658568 | 6/1995 |
|---|---|---|
| EP | 708179 | 4/1996 |
| WO | WO 91/11457 | 8/1991 |
| WO | WO 93/16105 | 8/1993 |
| WO | WO 93/18786 | 9/1993 |
| WO | WO 93/25579 | 12/1993 |
| WO | WO 95/05848 | 3/1995 |
| WO | WO 95/31214 | 11/1995 |
| WO | WO 96/05309 | 2/1996 |
| WO | WO 96/25487 | 2/1996 |
| WO | WO 96/29342 | 9/1996 |
| WO | WO 97/31943 | 9/1997 |
| WO | WO 98/05351 | 2/1998 |
| WO | WO 98/08871 | 3/1998 |
| WO | WO 98/08872 | 3/1998 |
| WO | WO 98/20895 | 5/1998 |

OTHER PUBLICATIONS

Aderlhorst et. al. J. Biol. Chem. 269:6275-6278, 1994.*
David et al., J. Biol. Chem. vol. 268, 17247-17252, 1993.*
Barbash, G. I., et al., "Significance of Diabetes Mellitus in Patients with Acute Myocardial Infarction Receiving Thrombolytic Therapy," (1993) JACC 22 (3) :707-713.
Begliner, C., Effect of Cholecystokinin on Gastric Motility in Humans, (1994) Ann NY Acad. Sci. 713:219-225.
Bevilacqua, S., et al., "Acute Elevation of Free Fatty Acid Levels Leads to Hepatic Insulin Resistance in Obese Subjects," (1987) Metabolism 36(5) :502-506.
Bevilacqua, S., et al., "Operation of Randle's Cycle in Patients With NIDDM," (1990) Diabetes 39:383-389.
Billington, C.J. and Levine, A.S., "Appetite regulation: Shedding New Light on Obesity," (1996) Current Biology 6(8):920-923.
Bing, C., et al., "the central regulation of energy homoeostasis: roles of neuropeptide Y and other brain peptides," (1996) Biochemical Society Transactions 24:559-565.
Bonadonna, R. C., et al., "Dose-dependent effect of insulin on plasma free fatty acid turnover and oxidation in humans," (1990) American Physiological Society :E736-E750.
Bonadonna, R. C., et al., "Time dependence of the interaction between lipid and glucose in humans," (1989) American Physiological Society: E49-E56.
Broderick, C. L., et al., "Abstract of Effect of sub-chronic administration of GLIP(7-37)OH on beta cell failure in Zucker diabetic rats," (1995) Dibetologia 38 (suppl.):A171.
Bullock, B.P., et al., "Tissue Distribution of Messenger Ribonucleic Acid Encoding the Rat Glucagon-Like Peptide-1 Receptor," (1996)_Endocrinology 137(7):2968-2978.
Chen, C.H. and Rogers, R.C., Central Inhibitory Action of Peptide YY on Gastric Motility in Rats, (1995) Am. J. Physiol. 269(4 Pt2):R787-792.
Chen, J.D., et al., "Inhibitory Effects of Chloecytokinin on Postprandial Gastric Myoelectrocal Activity," (1995) Dig. Dis. Sci.40(12): 2614-2622.
Chen, C.H. and Rogers, R.C., "PYY and NPY: Control of Gastric Motility Via Action on Y1 and Y2 Receptors in the DVC," (1997) Neurogastroenterol Motil 9(2): 109-116.
Coskun, T., et al., "Pathways mediating CRF-induced Inhibition of gastric Emptying in Rats," (1997) Regul. Pept. 69(3):113-130.
Davi, G., et al., "Thromboxane biosynthesis and platelet function in Type II diabetes mellitus," (1990) The New England Journal of Medicine, 322 (25):1769-1774.

(Continued)

Primary Examiner—Gary Nickol
Assistant Examiner—Gyan Chandra
(74) Attorney, Agent, or Firm—Gregory A. Cox; Mark J. Stewart

(57) ABSTRACT

This invention relates the use of glucagon-like peptides such as GLP-1, a GLP-1 analog, or a GLP-1 derivative in methods and compositions for reducing body weight.

8 Claims, No Drawings

OTHER PUBLICATIONS

Dhanvantari, S., et al., "Role of Prohormone Convertases in the Tissue-Specific Processing of Proglucagon," (1996) *Molecular Endocrinology* 10(4):342-355.

Doberne, L., et al., "Enhanced Glucose Utilization During Prolonged Glucose Clamp Studies," (1981) *Diabetes* 30:829-835.

Ferrannini, E., et al. "Effect of Fatty Acids on Glucose Production and Utilization in Man," (1983) *J. Clin. Invest.* 72 :1737-1747.

Fehmann, H., et al., "Glucagon-like peptide-1 (7-37) / (7-36) amide is a new incretin," (1992) *Molecular and Cellular Endocrinology* 85:C39-C44.

Frayn, K.N., I Hormonal control of metabolism in trauma and sepsis, (1986) *Clinical Endocrinology* 24:577-599.

Fuller, J. H., "Mortality trends and causes of death in diabetic patients," (1993) Diabete & *Metabolisme* 19:96-99.

Galuska, D., et al., "Effects of non-esterified fatty acids on insulin-stimulated glucose transport in isolated skeletal muscle from patients with type 2 (non-insulin-dependent) diabetes mellitus," (1994) Acta Diabetol 31:169-172.

Garvey, W. T., "Glucose Transport and NIDDM," (1992) *Diabetes Care* 15(3):396-417.

Gutniak, M. et al., Antidiabetogenic Effects of Glucagon-Like Peptide-1(7-36) Amide in Normal Subjects and Patients with Diabetes Mellitus: *New England Journal of Medicine*, vol. 326, No. 20, pp. 1316-1322, 1992.

Gutniak, M. K., et al., Subcutaneous Injection of the Incretin Hormone Glucagon-Like Peptide 1 Abolishes Postprandial Glycemia in NIDDM, (1994) *Diabetes Care* 17(9):1039-1044.

Hamann, A. And Matthaei, S., I Regulation of energy balance by leptin, (1996) *Exp. Clin. Endocrinal Diabetes* 104:293-300.

Hamilton, B.S., "A new role for a fat actor," (1996) *Nature Medicine* 2(3):272-273.

Higham, A., et al., "Relation Between Cholecystokinin and Antral Innervation in the Control of Gastric Emptying in the Rat" (1997) Gut 41(1):24-32.

International Search Report.

Jin, H., et al., "Secretin: A Physiological Regulator of Gastric Emptying and Acid Output in Dogs," (1994) Am. J. Physiol. 267(4 Pt 1) :G702-708.

Juntti-Berggren, L. et al., "Abstract of The antidiabetogenic effect of GLP-1 is maintained during a seven day treatment period and improves diabetic dyslipoproteinemia in NIDDM patients," :1-27.

Lambert, P. D.,et al, "A role for GLP-1(7-36)NH2 in the Central Control of Feeding Behaviour", *Digestion*, 54:360-361, 1994.

Larsen, J., et al., "One-Week Continuous Infusion of GLP-1(7-37) Improves the Glycaemic Control of NIDDM," (1996) *Diabet.* 45 (Supplement 2) :223A. Larsen, J., et al., abstract of "One-Week Continuous Infusion of GLP-1(7-37) Improves the Glycoemic Control in NIDDM," (1996) *Diabetes Abstract Book* 45 (Supp. 2):860.

Lu, Y. And Owyang, C. "Secretin at Physiological Doses Inhibits Gastric Motility Via a Vagal Afferent Pathway," (1995) *Am. J. Physiol.* 268 (6 Pt 1):G1012-6.

M. Navarro, et al., Changes in Food Intake Induced by GLP-1(7-36) amide in the Rat, *Abstracts of the 15th International Diabetes Federation Congress*, Nov. 6-11, 1994 Kobe, poster presentation 11A5PP1295.

M. Navarro, et al., "Colocalization of Glucagon-Like Peptide-1 (GLP-1) Receptors, Glucose Transporter GLUT-2, and Glucokinase mRNAs in Rat Hypothalamic Cells: Evidence for a Role of GLP-1 Receptor Agonists as an Inhibitory Signal for Food and Water Intake", *Journal of Neurochemistry*, vol. 67, No. 5, p. 1982-1991, 1996.

Nightingale, J.M., et al., "Gastrointestinal hormones in Short Bowel Syndrome. Peptide YY May be the 'Colonic Brake' to Gastric Emptying," (1996) Gut 39(2):267-272.

Raybould, H.E. And Holtzer, H., "Secretin Inhibits Gastirc Emptying in Rats Via a Capsaicin-Sensitive Vagal Afferent Pathway," (1993) *Eur. J. Pharmacol.* 250(1):165-167.

Schick,R., et al., "Glucagon-like peptide 1—a novel brain peptide involved in feeding regulation", *Obesity in Europe*, Chapter 53, pp. 363-367, 1993.

Schwizer, W., et al. "Role of Cholecystokinin in the Regulation of Liquid Gastric Emptying and Gastric Motility in Humans: Studies with the CCK Antagonist Loxiglumide," (1997) Gut 41(4):500-504.

Serradas, P., et al., Abstract GLP-1 confers glucose sensitivity to previously glucose-resistant B cells in a rat model of non insulin dependent diabetes, Diabetologia (1995).

Takahashi, T. And Owyang, C., "Mechanism of Cholecytokinin-Induced Relation of the Rat Stomach," 1999) J. Auton. Nerv. *Syst.* 75(2-3):123-130.

Tang-Christensen, et al., Central administration of GLP-1-(7-36) amide inhibits food and water intake in rats, *American Journal Physiological*, 271:R848-R856, 1996.

Thompson, R.G., et al., Pramlintide, a Synthetic Analog of Human Amylin, Improves the Metabolic Profile of Patients with Type 2 Diabetes Using Insulin, (1998) *Diebet. Care* 21(6):987-993.

Turton, M.S., et al., "A role for glucagon-like peptide-1 in the central regulation of feeding," (1996) Nature 379:69-72.

Wang, Z., et al., "Glucagon-like Peptide-1 is a Physiological Incretin in Rat,"(1995) *J. Clin. Invest.* 95:417-421.

Weber, I., et al., "Abstract of Prolonged normalization of fasting glycaemia by intravenous GLP-1([7-36 amide] or [7-37]) in Type 2-diabetic patients," (1995) Diabetologia 38 (suppl) :A171.

Wettergren, A. et al., "Truncated GLP-1 (Proglucagon 78-107-Amide) Inhibits Gastric and Pancreatic Functions in Man", *Digestive Diseases and Sciences*, vol. 38, No. 4, pp. 665-673, 1993.

Wheeler, M. B. et al., "Functional Expression of the Rat Glucagon-Like Peptide-I Receptor, Evidence for Coupling to both Adenylyl Cyclase and Phospholipase-C," (*1993*) *Endocrinology* 133(1):57-62.

Wiley, J.W., et al., "Mechanism of Action of peptide Y to Inhibit Gastric Motility" (1991) Gastroenterol 100(4):865-872.

Willms, B., et al., "Gastric Emptying, Glucose Responses, and Insulin Secretion after a Liquid Test Meal: Effects of Exogenous Glucagon-Like Peptide-I (GLP-1)—(7-36) Amide in Type 2 (Noninsulin-Dependent) Diabetic Patients," (1996) *Journal of Clinical Endocrinology and Metabolism* 81(1) :327-332.

Wojdemann, M. et al., "Glucagon-like Peptide-2 Inhibits Centrally Induced Antral Motility in Pigs," *Scand. J. Gastrocontrol.* 33(8) :828-832.

Wolffenbuttel, B.H.R. And Van Haeften, T.W., Prevention of Complications in Non-Insulin-Dependent Diabetes Mellitus (NIDDM), (1995) *Drugs* 50(2):263-288.

Yoshimoto, T., et al., "Modulation of Vascular Natriuretic Peptide Receptor Gene Expression in Hypertensive and Obese Hyperglycemic Rats," (1995) Endocrinology 136(6) :2427-2434.

Zai, H. et al., "Effect of Peptide YY on Gastric Motor and Secretory Activity in Vagally Innervated and Denervated Corpus Pouch Dogs," (1996) *Regul. Papr.* 61(3):181-188.

Zandomeneghi, R., et al., "Abstract of Possible metabolic significance of the rectal localized glucagon like peptide 1 (78-37)," (1995) Diabetologia 38(suppl.):A171.

Zinman, B., et al., "Abstract of Insulin Lispro in CSII: Results of a Double-Blind Cross-Over Study," :1-18.

* cited by examiner

USE OF GLP-1 ANALOGS AND DERIVATIVES ADMINISTERED PERIPHERALLY IN REGULATION OF OBESITY

This Application is a Continuation Application of U.S. Ser. No. 09/585,186, filed Jun. 1, 2000 now U.S. Pat. No. 6,583,111, which is a Continuation of U.S. Ser. No. 08/961,405, filed Oct. 30, 1997 now U.S. Pat. No. 6,191,102, which claims the benefit of U.S. Provisional Application No. 60/030,213, filed Nov. 5, 1996.

BACKGROUND OF THE INVENTION

This invention relates to the use of glucagon-like peptide-1 (GLP-1), analogs and derivatives of GLP-1, in methods and compositions, in particular pharmaceutical formulations, that promote weight-loss.

Obesity, and especially upper body obesity, is the most common nutritional disorder in the over-nourished populations of the world. Numerous studies indicate that lowering body weight dramatically reduces risk for chronic diseases, such as diabetes, hypertension, hyperlipidemia, coronary heart disease, and musculoskeletal diseases. For example, various measures of obesity, including, simple body weight, waist-to-hip ratios, and mesenteric fat depot, are strongly correlated with risk for non-insulin dependent diabetes (NIDDM), also known as type II diabetes. According to the American Diabetes Association (1995) about 80% of NIDDM patients are overweight. Weight-reduction is a specific goal of medical treatment of many chronic diseases, including NIDDM.

Current methods for promoting weight loss are not completely satisfactory. Some obese patients may lose weight through deliberate modification of behavior, such as changing diet and increased exercise. Failure to achieve weight loss by these methods may be due to genetic factors that cause increased appetite, a preference for high-fat foods, or a tendency for lipogenic metabolism. Unfortunately, an estimated 33 billion dollars a year are spent on weight-loss measures that are largely futile. Thus, new methods and compositions such as pharmaceutical agents that promote weight-loss are urgently needed to complement old approaches.

Glucagon-like peptide 1 (GLP-1) is known to play a critical role in the regulation of the physiological response to feeding. GLP-1 is processed from proglucagon and is released into the blood from the endocrine L-cells mainly located in the distal small intestine and colon in response to ingestion of a meal (Nilsson et al., 1991; Krcymann et al., 1987; Mojsov et al. 1986). GLP-1 acts through a G protein-coupled cell surface receptor (GLP-1R) and enhances nutrient-induced insulin synthesis (Fehmann et al, 1992) and release (Fehmann et al., 1995). GLP-1 stimulates insulin secretion (insulinotropic action) and cAMP formation (Mojsov et al., 1992). GLP-1(7-36) amide stimulates insulin release, lowers glucagon secretion, and inhibits gastric secretion and emptying (Nauck, 1993; Gutniak et al, 1992). These gastrointestinal effects of GLP-1 are not found in vagotomized subjects, pointing to a centrally-mediated effect (Orskov et al., 1995). GLP-1 binds with high affinity to isolated rat adipocytes, activating cAMP production (Valverde et al., 1993) and stimulating lipogenesis (Oben, et al., 1991) or lipolysis (Ruiz-Grande et al., 1992). GLP-1 stimulates glycogen synthesis, glucose oxidation, and lactate formation in rat skeletal muscle (Villanueva et al., 1994).

m-RNA encoding the pancreatic-type GLP-1 receptor is found in relatively high quantities in rat pancreatic islets, lung, hypothalamus, and stomach (Billock et al., 1996). Interestingly, despite the knowledge that both GLP-1 and GLP-1 receptors are found in the hypothalamus (Krcymann et al., 1989; Kanse et al., 1988), no central role for GLP-1 was determined until a recent report that GLP-1 administered by the intracerebroventricular route (ICV) markedly inhibits feeding in fasted rats (Turton et al., 1996). The same report indicates that after ICV administration of GLP-1, c-fos, a marker of neuronal activation, appears exclusively in the paraventricular nucleus of the hypothalamus and in the central nucleus of the amygdala, two regions of the brain of primary importance in the regulation of feeding (Morley, 1987). ICV GLP-1 also significantly reduces food intake following injection of the powerful feeding stimulant, neuropeptide Y, in animals fed ad libitum (Turton et al., 1996). A subsequent report demonstrates that GLP-1 administered centrally or peripherally is involved in control of body temperature regulation, but does not affect food intake after acute intraperitoneal administration in rats (O'Shea et al., 1996). A recent article reports that lateral ventricular injections of GLP-1 in sated rats induce extensive stimulation of Fos-ir in the paraventricular nucleus and parvocellular central nucleus of the amygdala, substantiating Turton, et al. (Rowland et al., 1996). Additionally, these investigators described strong activation of other centers involved in the regulation of feeding, including the immediate early gene protein product in the nucleus of the tractus solitarius, the pontine lateral parabrachial nucleus, the basal nucleus of the stria terminals, and the area postrema. GLP-1 receptors accessible to peripheral GLP-1 are found in the rat subfornical organ and area postrema (Orskov et al., 1996).

Turton et al. (1996) specifically state that the effects of GLP-1 on body weight and food intake are caused only by administration of GLP-1 directly in the cerebroventriculum, that intraperitoneal administration of GLP-1, even at relatively high does, does not affect early dark-phase feeding, and that GLP-1 fragments are inactive when administered peripherally, citing (Suzuki et al., 1989). Such statements discourage the use of GLP-1 as a composition (pharmaceutical agent) for reducing body weight, because central routes of administration, such as the ICV route, are not feasible for treating obesity in humans. The physiological effects of GLP-1 documented above have led to the suggestion of its beneficial use for treating diabetes and obesity by transplanting recombinant cell lines encoding GLP-1 or GLP or GLP-1 receptors, for example (WO 96/25487)

Another publication discouraged the use of GLP-1 by interpreting the art to show that "peripheral administration of GLP-1 had no effect on feeding behavior." (WO 97/31943, page 3). This publication also reported an effect of GLP-2 on food intake when administered peripherally.)

SUMMARY OF THE INVENTION

Methods and compositions, in particular pharmaceutical formulations, medicaments, using glucagon-like peptide-1 analogs, derivatives, and active peptides thereof, are effective in reducing body weight and in treating obesity. The definition of obesity varies with geographical location, clinical focus, and social preferences. The methods and compositions of the present invention, however, are suitable for any subject in which weight reduction is desired. The invention is not limited for use in, e.g. diabetic patients.

Peripheral administration of GLP-1 (7-36) amide to obese patients quite unexpectedly, and contrary to the implications of Turton et al. (1996), causes a significant reduction in body weight. Thus, an aspect of the present invention is a method of reducing body weight which includes preparing a composition having a glucagon-like peptide-1 compound and administering it to a subject. Suitable glucagon-like peptide-1 compounds include GLP-1, GLP-1 analogs, GLP-1 derivatives, agonists of the GLP-1 receptor, agonists of the GLP-1 signal transduction cascade, compounds that stimulate synthesis of endogenous GLP-1, compounds that stimulate release of endogenous GLP-1, and pharmaceutically-acceptable salts thereof. A pharmaceutically effective dose, that is, a dose sufficient to cause reduction in body weight, is administered.

DETAILED DESCRIPTION OF THE INVENTION

Methods and compositions, in particular medicaments (pharmaceutical compositions or formulations) using glucagon-like peptide-1, analogs or derivatives thereof, are effective in reducing body weight and in treating obesity. Analogs and derivatives of GLP-1 that are useful for the practice of the invention are those with an increased half life compared to GLP-1 and the ability to effect weight loss when administered to a subject over a period of time. The definition of obesity varies with geographical location, clinical focus, and social preferences. The methods and compositions of the present invention, however, are suitable for any subject in which weight reduction is desired. The invention is not limited for use in, e.g. diabetic patients.

Compounds

GLP-1 analogs, derivatives, variants, precursors and homologues are all suitable for the practice of the invention as long as the active fragment that effects weight loss is included.

"GLP-1" means GLP-1(7-37). By custom in the art, the amino-terminus of GLP-1(7-37) has been assigned number 7 and the carboxy-terminus, number 37. The amino acid sequence of GLP-1(7-37) is well-known in the art, but is presented below for the reader's convenience:

(SEQ ID NO:1)
NH$_2$-His$^7$-Ala-Glu-Gly$^{10}$-

Thr-Phe-Thr-Ser-Asp$^{15}$-Val-Ser-Ser-Tyr-Leu$^{20}$-

Glu-Gly-Gln-Ala-Ala$^{25}$-Lys-Glu-Phe-Ile-Ala$^{30}$-

Trp-Leu-Val-Lys-Gly$^{35}$-Arg-Gly$^{37}$-COOH

A "GLP-1 analog" is defined as a molecule having a modification including one or more amino acid substitutions, deletions, inversions, or additions when compared with GLP-1. GLP-1 analogs known in the art include, for example, GLP-1(7-34) and GLP-1(7-35), GLP-1(7-36), Val$^8$-GLP-1(7-37), Gln$^9$-GLP-1(7-37), D-Gln$^9$-GLP-1(7-37), Thr$^{16}$-Lys$^{18}$-GLP-1(7-37), and Lys$^{18}$-GLP-1(7-37). Preferred GLP-1 analogs are GLP-1(7-34) and GLP-1(7-35), which are disclosed in U.S. Pat. No. 5,118,666, and also GLP-1(7-36). These compounds are the biologically processed forms of GLP-1 having insulinotropic properties. Other GLP-1 analogs are disclosed in U.S. Pat. No. 5,545,618.

A "GLP-1 derivative" is defined as a molecule having the amino acid sequence of GLP-1 or of a GLP-1 analog, but additionally having at least one chemical modification of one or more of its amino acid side groups, a-carbon atoms, terminal amino group, or terminal carboxylic acid group. A chemical modification includes adding chemical moieties, creating new bonds, and removing chemical moieties. Modifications at amino acid side groups include acylation of lysine e-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a C$_1$–C$_4$ alkyl. Furthermore, one or more side groups, or terminal groups, may be protected by protective groups known to the ordinarily-skilled protein chemist. The α-carbon of an amino acid may be mono- or di-methylated.

In the present invention a preferred group of GLP-1 analogs and derivatives for use in the present invention is composed of the various GLP-1 molecules claimed in U.S. Pat. No. 5,545,618 ('618). Effective analogs of the active GLP-1 peptides, 7-34, 7-35, 7-36 and 7-37 have amino acid substitutions as positions 7-10 and/or are truncated at the C-terminus and/or contain various other amino acid substitutions in the basic peptide. Analogs having D-amino acid substitutions in the 7 and 8 positions and/or N-alkylated or N-acylated amino acids in the 7 position are particularly resistant to degradation in vivo.

The analogs of the invention in '618 which show enhanced insulin stimulating properties have the sequence, of native GLP-1, 7-34, 7-35, 7-36, or 7-37, or the C-terminal amide thereof, with at least one modification selected from the group consisting of:

(a) substitution of a neutral amino acid, arginine, or a D form of lysine for lysine at position 26 and/or 34 and/or a neutral amino acid, lysine, or a D form of arginine for arginine at position 36;

(b) substitution of an oxidation-resistant amino acid for tryptophan at position 31;

(c) substitution according to at least one of:
Y for V at position 16;
K for S at position 18;
D for E at position 21;
S for G at position 22;
R for Q at position 23;
R for A at position 24; and
Q for K at position 26;

(Using the single letter codes for amino acids)
(d) a substitution comprising at least one of:
an alternative small neutral amino acid for A at position 8;
an alternative acidic amino acid or neutral amino acid for E at position 9;
an alternative neutral amino acid for G at position 10; and
an alternative acidic amino acid for D at position 15; and
(e) substitution of an alternative neutral amino acid or the D or N-acylated or alkylated form of histidine for histidine at position 7.

With respect to modifications (a), (b), (d) and (e), the substituted amino acids may be in the D form. The amion acids substituted at position 7 can also be in the N-acylated or N-alkylated forms.

In another aspect, the invention of '618 is directed to peptides which show enhanced degradation resistance in plasma as compared to GLP-1 (7-37) wherein this enhanced resistance to degradation. In these analogs, any of the above-mentioned truncated forms of GLP-1(7-34) to GLP-1(7-37) or their C-terminal amidated forms is modified by (a) substitution of a D-neutral or D-acidic amino acid for H at position 7, or (b) substitution of a D-amino acid for A at position 8, or (c) both, or (d) substitution of an N-acylated or N-alkylated form of any naturally occurring amino acid for H at position 7.

Thus analogs which are resistant to degradation include (N-acyl (1–6C) AA)$^7$ GLP-1(7-37) and (N-alkyl (1–6C AA)$^7$ GLP-1(7-37) wherein when AA is a lysyl residue, one or both nitrogens may be alkylated or acylated, AA symbolizes any amino acid consistent with retention of insulin stimulating activity.

For substitutions of D-amino acids in the 7 and 8 positions, the D residue of any acidic or neutral amino acid can be used at position 7 and of any amino acid at position 8, again consistent with insulin stimulating activity. Either or both of position 7 and 8 can be substituted by a D-amino acid; the D-amino acid at position 7 can also be acylated or alkylated. These modified forms are applicable not only to GLP-1(7-37) but also to shorter truncated analogs.

Thus, among the preferred analogs of the '618 invention are those wherein the (7-34), (7-35), or (7-37) form of GLP-1 has been modified only by substitution of a neutral amino acid, arginine, or a D form of lysine for lysine at position 26 and/or 34 and/or a neutral amino acid, lysine, or a D form of arginine for arginine at position 36 (section (a)). Particularly preferred are those wherein the amino acid substituted for lysine at position 26 and 34 is selected from the group consisting of K$^+$, G, S, A, L, I, Q, R, R$^+$ and M, and for arginine at position 36 is selected from the group of K, K$^+$, G, S, A, L, I, Q, M, and R$^+$. (where $^+$ indicates a D form).

Also preferred are analogs wherein the sole modification is the substitution of an oxidation-resistant amino acid for tryptophan at position 31 (section (b)). Particularly favored substitutions are selected from the group consisting of F, V, L, I, A, and Y.

Also preferred are those analogs wherein the only modification is at least one of those specific substitutions set forth in section (c). Particularly preferred are those analogs wherein combined substitutions of S for G at position 22, R at positions 23 and 24 for Q and A respectively, and Q for K at position 26 have been made, or substitutions of Y for V at position 16 and K for S at position 18 have been made, or these substitutions plus D for E at positions 21 have been made.

Also preferred are analogs wherein the sole modifications are those set forth in section (d). Particularly preferred among these are those wherein the small neutral amino acid substituted for alanine at position 8 is selected from the group consisting of S, S$^+$, GC, C$^+$, Sar, A$^+$, beta-ala and Aib; and/or the acidic or neutral amino acid substituted for glutamic acid at position 9 is selected from the group consisting of E$^+$, D, D$^+$, Cya T, T$^+$, N, N$^+$, Q, Q$^+$, Cit, MSO, and acetyl-K; and/or the alternative neutral amino acid substituted for glycine at position 10 is selected from the group consisting of S, S$^+$, Y, Y$^+$, T, T$^+$, N, N$^+$, Q, Q$^+$, Cit, MSO, acetyl-K, F, and F+; and/or wherein D is substituted for E at position 15.

Also preferred are analogs wherein position 7 alone has been altered (section (e)). Preferred substitutions are those wherein the amino acid substituted for histidine at position 7 is selected from the group consisting of H$^+$, Y, Y$^+$, F, F$^+$, R, R$^+$, Orn, Orn$^+$, M, M$^+$, N-formyl-H, N-formyl-H $^+$, N-acetyl-H, N-acetyl-H$^+$, N-isopropyl-H, N-isopropyl-H$^+$, N-acetyl-K; N-acetyl-K$^+$, P and P$^+$.

Also preferred are embodiments with a combination of only two of the above-referenced classes of modified forms, in addition to the following specific embodiments.

The following specific analogs are preferred:

(H$^+$)$^7$-GLP-1(7-37);
(Y)$^7$-GLP-1(7-37);
(N-acetyl-H)$^7$-GLP-1(7-37);
(N-isopropyl-H)$^7$-GLP-1 (7-37);
(A$^+$)$^8$-GLP-1(7-37);
(E$^+$)$^9$-GLP-1(7-37);
(D)$^9$-GLP-1(7-37);
(D$^+$)$^9$-GLP-1(7-37);
(F$^+$)$^{10}$-GLP-1(7-37);
(S)$^{22}$(R)$^{23}$(R)$^{24}$(Q)$^{26}$-GLP-1(7-37);
(S)$^8$(Q)$^9$(Y)$^{16}$(K)$^{18}$(D)$^{21}$-GLP-1(7-37)

Preferred forms of analogs with enhanced stability also have only one, or at most two, amino acid modifications.

Preferred substitutions for the histidine at position 7 include the D-forms of acidic or neutral amino acids or the D-forms of histidines. Preferred are P$^+$, D$^+$, E$^+$, N$^+$, Q$^+$, L$^+$, V$^+$, I$^+$and H$^+$.

The histidine at position 7, or a replacement (D or L), can also be N-alkylated (1–6C) or N-acylated (1–6C). Alkyl groups are straight or branched chain (including cyclic) hydrocarbyl residues of the indicated member of C. Acyl groups are of the formula RCO-wherein R is alkyl. Preferred alkyl groups are t-propyl, α-propyl and ethyl; preferred acyl are acetyl and propionyl. Preferred residues which may be alkylated or acylated include P, D, E, N, Q, V, L, I, K and H in either the D or L form.

Preferred substitutions for alanine at position 8 are the D-forms of P, V, L, I and A; also preferred are the D-forms of D, E, N, Q, K, T, S and H.

Some specific analogs show both enhanced insulin release stimulating activity and enhanced stability.

A preferred group of GLP-1 analogs and derivatives for use in the present invention is composed of molecules of the formula:

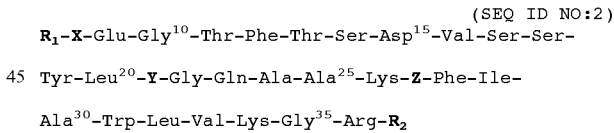

```
                                                    (SEQ ID NO:2)
R₁-X-Glu-Gly¹⁰-Thr-Phe-Thr-Ser-Asp¹⁵-Val-Ser-Ser-

Tyr-Leu²⁰-Y-Gly-Gln-Ala-Ala²⁵-Lys-Z-Phe-Ile-

Ala³⁰-Trp-Leu-Val-Lys-Gly³⁵-Arg-R₂
``` and the pharmaceutically-acceptable salts thereof, wherein: R$_1$ is selected from the group consisting of L-histidine, D-histidine, desamino-histidine, 2-amino-histidine, b-hydroxy-histidine, homohistidine, alpha-fluoromethyl-histidine, and alpha-methyl-histidine; X is selected from the group consisting of Ala, Gly, Val, Thr, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and R$_2$ is selected from the group consisting of NH$_2$, and Gly-OH; provided that the compound has an isoelectric point in the range from about 6.0 to about 9.0 and further providing that when R$_1$ is His, X is Ala, Y is Glu, and Z is Glu, R$_2$ must be NH$_2$.

Numerous GLP-1 analogs and derivatives having an isoelectric point in the range from about 6.0 to about 9.0 have been disclosed and include, for example:

GLP-1 (7-36)NH$_2$
Gly$^8$-GLP-1 (7-36)NH$_2$
Gln$^9$-GLP-1 (7-37)

D-Gln⁹-GLP-1 (7-37)

acetyl-Lys⁹-GLP-1 (7-37)

Thr⁹-GLP-1 (7-37)

D-Thr⁹-GLP-1 (7-37)

Asn⁹-GLP-1 (7-37)

D-Asn⁹-GLP-1 (7-37)

Ser²²-Arg²³-Arg²⁴-Gln²⁶-GLP-1 (7-37)

Thr¹⁶-Lys¹⁸-GLP-1 (7-37)

Lys¹⁸-GLP-1 (7-37)

Arg²³-GLP-1 (7-37)

Arg²⁴-GLP-1 (7-37)

Another preferred group of active compounds for use in the present invention is disclosed in WO 91/11457, (related to U.S. Pat. No. 5,545,618) and includes GLP-1(7-34), GLP-1(7-35), GLP-1(7-36), or GLP-1(7-37), or the amide form thereof, and pharmaceutically-acceptable salts thereof, having at least one modification including those shown below:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, (Mentlein et al., 1993), administration of GLP-1 analogs and derivatives that are protected from the activity of DPP IV is preferred, and the administration of Gly⁸-GLP-1(7-36)NH₂, Val⁸-GLP-1(7-37)OH, a-methyl-Ala⁸-GLP-1(7-36)NH₂, and Gly⁸-Gln²¹-GLP-1(7-37)OH, or pharmaceutically-acceptable salts thereof, is more preferred.

The use in the present invention of a molecule claimed in U.S. Pat. No. 5,188,666 ('666) is also preferred. Such a molecule includes a peptide having one of the following amino acid sequences:

(SEQ ID NO:3)
NH₂-His⁷-Ala-Glu-Gly¹⁰-Thr-Phe-Thr-Ser-Asp¹⁵-Val-

Ser-Ser-Tyr-Leu²⁰-Glu-Gly-Gln-Ala-Ala²⁵-Lys-Glu-

Phe-Ile-Ala³⁰-Trp-Leu-Val-X wherein X may be Lys and Lys-Gly; or a derivative of said peptide, and wherein said peptide may be a pharmaceutically-acceptable acid addition salt of said peptide; a pharmaceutically-acceptable carboxylate salt of said peptide; a pharmaceutically-acceptable lower alkylester of said peptide; or a pharmaceutically-acceptable amide of said peptide selected from the group consisting of amide, lower alkyl amide, and lower dialkyl amide.

The invention in '666 pertains to a peptide fragment which is insulinotropic and is derivable from a naturally occurring amino acid sequence.

The invention comprises a compound selected from the group consisting of:

(A) a peptide comprising the sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X wherein X is selected form the group consisting of:
(a) Lys,
(b) Lys-Gly,
(c) Lys-Gly-Arg;

and (B) a derivative of the peptide; wherein the compound is substantially free of natural contaminants, and has an insulinotropic activity which exceeds the insulinotropic activity of GLP-1 (1-36) or GLP-1 (1-37).

The invention also includes a compound selected from the group consisting of:

(A) a peptide comprising the sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X wherein X is selected form the group consisting of:
(a) Lys,
(b) Lys-Gly,
(c) Lys-Gly-Arg;

and (B) a derivative of the peptide; wherein the compound is substantially free of natural contaminants, and has an insulinotropic activity at a concentration of at least 10⁻¹⁰M.

Of particular interest are peptides of the following formula:

$$H_2N-X-CO-R^1 \quad (1)$$

wherein $R^1$ is OH, OM, or $-NR^2R^3$;

M is a pharmaceutically acceptable cation or a lower branched or unbranched alkyl group;

$R^2$ and $R^3$ are the same or different and selected from the group consisting of hydrogen and a lower branched or unbranched alkyl group;

X is a peptide comprising the sequence:
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg $NH^2$ is the amine group of the amino terminus of X; and CO is the carbonyl group of the carboxy terminus of X;

(2) the acid addition salts thereof; and (3) the protected or partially protected derivatives thereof;

wherein said compound has an insulinotropic activity which exceeds the insulinotropic activity of GLP-1 (1-36) or GLP-1 (1-37).

Another preferred group of molecules for use in the present invention consists of compounds claimed in U.S. Pat. No. 5,512,549 having the general formula:

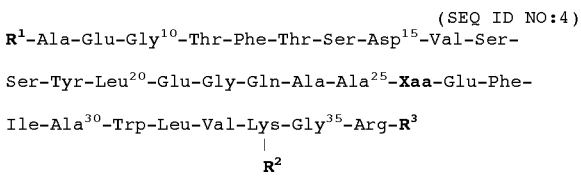
(SEQ ID NO:4)
R$^1$-Ala-Glu-Gly$^{10}$-Thr-Phe-Thr-Ser-Asp$^{15}$-Val-Ser-Tyr-Leu$^{20}$-Glu-Gly-Gln-Ala-Ala$^{25}$-Xaa-Glu-Phe-Ile-Ala$^{30}$-Trp-Leu-Val-Lys-Gly$^{35}$-Arg-R$^3$
|
R$^2$ and pharmaceutically-acceptable salts thereof, wherein R$^1$ may be 4-imidazopropionyl, 4-imidazoacetyl, or 4-imidazo-a, a dimethyl-acetyl; R$^2$ may be $C_6$–$C_{10}$ unbranched acyl, or absent; R$^3$ may be Gly-OH or NH$_2$; and, Xaa is Lys or Arg.

More preferred compounds of SEQ ID NO:4 for use in the present invention are those in which Xaa is Arg and R$^2$ is a $C_6$–$C_{10}$ unbranched acyl.

Highly preferred compounds of SEQ ID NO:4 for use in the present invention are those in which Xaa is Arg, R$^2$ is $C_6$–$C_{10}$ unbranched acyl, and R$^3$ is Gly-OH.

More highly preferred compounds of SEQ ID NO:4 for use in the present invention are those in which Xaa is Arg, R$^2$ is a $C_6$–$C_{10}$ unbranched acyl, R$^3$ is Gly-OH, and R$^1$ is 4-imidazopropionyl.

The most preferred compound of SEQ ID NO:4 for use in the present invention is that in which Xaa is Arg, R$^2$ is $C_8$ unbranched acyl, R$^3$ is Gly-OH, and R$^1$ is 4-imidazopropionyl.

The use in the present invention of a molecule claimed in U.S. Pat. No. 5,120,712 is highly preferred. Such a molecule includes a peptide having the amino acid sequence:

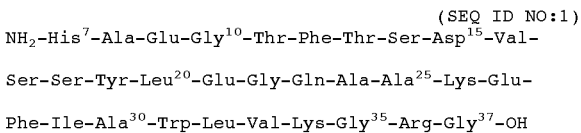
(SEQ ID NO:1)
NH$_2$-His$^7$-Ala-Glu-Gly$^{10}$-Thr-Phe-Thr-Ser-Asp$^{15}$-Val-Ser-Ser-Tyr-Leu$^{20}$-Glu-Gly-Gln-Ala-Ala$^{25}$-Lys-Glu-Phe-Ile-Ala$^{30}$-Trp-Leu-Val-Lys-Gly$^{35}$-Arg-Gly$^{37}$-OH and a derivative of said peptide, wherein said peptide may be a pharmaceutically-acceptable acid addition salt of said peptide; a pharmaceutically-acceptable carboxylate salt of said peptide; a pharmaceutically-acceptable lower alkylester of said peptide; or a pharmaceutically-acceptable amide of said peptide wherein the amide may be an amide, lower alkyl amide, or lower dialkyl amide.

The use of GLP-1(7-36) amide, or a pharmaceutically-acceptable salt thereof, in the present invention is most highly preferred. The amino acid sequence of GLP-1(7-36) amide is:

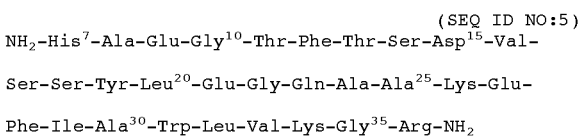
(SEQ ID NO:5)
NH$_2$-His$^7$-Ala-Glu-Gly$^{10}$-Thr-Phe-Thr-Ser-Asp$^{15}$-Val-Ser-Ser-Tyr-Leu$^{20}$-Glu-Gly-Gln-Ala-Ala$^{25}$-Lys-Glu-Phe-Ile-Ala$^{30}$-Trp-Leu-Val-Lys-Gly$^{35}$-Arg-NH$_2$ The use of Val$^8$-GLP-1(7-37)OH, or a pharmaceutically-acceptable salt thereof, in the present invention is most highly preferred. The amino acid sequence of Val$^8$-GLP-1 (7-37)OH is:

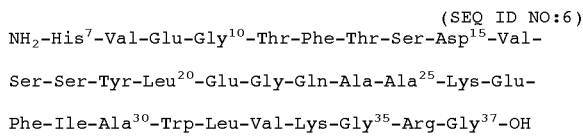
(SEQ ID NO:6)
NH$_2$-His$^7$-Val-Glu-Gly$^{10}$-Thr-Phe-Thr-Ser-Asp$^{15}$-Val-Ser-Ser-Tyr-Leu$^{20}$-Glu-Gly-Gln-Ala-Ala$^{25}$-Lys-Glu-Phe-Ile-Ala$^{30}$-Trp-Leu-Val-Lys-Gly$^{35}$-Arg-Gly$^{37}$-OH Preparation of the Compounds Methods for preparing the active compounds used in the present invention, namely, GLP-1, an GLP-1 analog, or a GLP-1 derivative, or any related compound including an active fragment effecting weight loss when administered peripherally, are well-known, and are described in U.S. Pat. Nos. 5,118,666, 5,120,712, and 5,523,549.

The amino acid portion of the active compound used in the present invention, or a precursor thereto, is made by 1) solid-phase synthetic chemistry; 2) purification of GLP molecules from natural sources; 3) recombinant DNA technology; or 4) a combination of these methods.

Solid phase chemical synthesis of polypeptides is well known in the art and may be found in general texts in the area such as Dugas and Penney 1981; Merrifield 1962; Stewart and Young 1969.

For example, the amino acid portion may be synthesized by solid-phase methodology utilizing a 430A peptide synthesizer (PE-Applied Biosystems, Inc., 850 Lincoln Center Drive, Foster City, Calif. 94404) and synthesis cycles supplied by PE-Applied Biosystems. BOC-amino acids and other reagents are commercially available from PE-Applied Biosystems and other chemical supply houses. Sequential BOC chemistry using double couple protocols are applied to the starting p-methyl benzhydryl amine resins for the production of C-terminal carboxamides. For the production of C-terminal acids, the corresponding PAM resin is used. Asn, Gln, and Arg are coupled using preformed hydroxy benzotriazole esters. The following side chain protecting groups may be used:

Arg, Tosyl
Asp, cyclohexyl
Glu, cyclohexyl
Ser, Benzyl
Thr, Benzyl
Tyr, 4-bromo carbobenzoxy BOC deprotection may be accomplished with trifluoroacetic acid in methylene chloride. Following completion of the synthesis the peptides may be deprotected and cleaved from the resin with anhydrous hydrogen fluoride (HF) containing 10% meta-cresol. Cleavage of the side chain protecting group(s) and of the peptide from the resin is carried out at −5° C. to 5° C., preferably on ice for 60 minutes. After removal of the HF, the peptide/resin is washed with ether, and the peptide extracted with glacial acetic acid and lyophilized.

Techniques well-known to the ordinarily-skilled artisan in recombinant DNA technology may be used to prepare the active compound used in present invention. In fact, recombinant DNA methods may be preferable because of higher yield. The basic steps in recombinant production are:

a) isolating a natural DNA sequence encoding a GLP-1 molecule of the present invention or constructing a synthetic or semi-synthetic DNA coding sequence for a GLP-1 molecule, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 molecule, and e) recovering and purifying the recombinantly produced GLP-1 molecule.

As previously stated, the coding sequences may be wholly synthetic or the result of modifications to the larger, native glucagon-encoding DNA. A DNA sequence that encodes preproglucagon is presented in Lund et al. 1982 and may be used as starting material in the semisynthetic production of the compounds of the present invention by altering the native sequence to achieve the desired results.

Synthetic genes, the in vitro or in vivo transcription and translation of which results in the production of a GLP-1 molecule, may be constructed by techniques well known in the art. Owing to the natural degeneracy of the genetic code, the skilled artisan will recognize that a sizable yet definite number of DNA sequences may be constructed, all of which encode GLP-1 molecules of the present invention.

The methodology of synthetic gene construction is well-known in the art (Brown et al. 1979.) The DNA sequence is designed from the desired amino acid sequence using the genetic code, which is easily ascertained by the ordinarily-skilled biologist. Once designed, the sequence itself may be generated using conventional DNA synthesizing apparatus such as the Model 380A or 380B DNA synthesizers (PE-Applied Biosystems, Inc., 850 Lincoln Center Drive, Foster City, Calif. 94404).

To express the amino acid portion of a compound used in the present invention, an engineered synthetic DNA sequence is inserted in any one of many appropriate recombinant DNA expression vectors through the use of appropriate restriction endonucleases (Maniatis et al., 1989). Restriction endonuclease cleavage sites are engineered into either end of the GLP-1 molecule-encoding DNA to facilitate isolation from, and integration into, amplification and expression vectors well-known in the art. The particular endonucleases employed will be dictated by the restriction endonuclease cleavage pattern of the parent expression vector employed. Restriction sites are chosen to properly orient the coding sequence with control sequences, thereby achieving proper in-frame reading and expression of the protein of interest. The coding sequence must be positioned to be in proper reading frame with the promoter and ribosome binding site of the expression vector, both of which are functional in the host cell in which the protein is to be expressed.

To achieve efficient transcription of the synthetic gene, it must be operably associated with a promoter-operator region. Therefore, the promoter-operator region of the synthetic gene is placed in the same sequential orientation with respect to the ATG start codon of the synthetic gene.

A variety of expression vectors useful for transforming prokaryotic and eukaryotic cells are well known in the art (Promega Catalogue, 1992; Stratagene Catalogue, 1992). Also, U.S. Pat. No. 4,710,473 describes circular DNA plasmid transformation vectors useful for expression of exogenous genes in *E. coli* at high levels. These plasmids are useful as transformation vectors in recombinant DNA procedures and (a) confer on the plasmid the capacity for autonomous replication in a host cell;

(b) control autonomous plasmid replication in relation to the temperature at which host cell cultures are maintained;

(c) stabilize maintenance of the plasmid in host cell populations;

(d) direct synthesis of a protein product indicative of plasmid maintenance in a host cell population;

(e) provide in-series restriction endonuclease recognition sites unique to the plasmid; and (f) terminate mRNA transcription.

These circular DNA plasmids are useful as vectors in recombinant DNA procedures for securing high levels of expression of exogenous genes.

Having constructed an expression vector for the amino acid portion of a compound used in the present invention, the next step is to place the vector into a suitable cell and thereby construct a recombinant host cell useful for expressing the polypeptide. Techniques for transforming cells with recombinant DNA vectors are well known in the art and may be found in such general references as Maniatis, et al. supra. Host cells made be constructed from either eukaryotic or prokaryotic cells.

Prokaryotic host cells generally produce the protein at higher rates and are easier to culture. Proteins expressed in high-level bacterial expression systems characteristically aggregate in granules or inclusion bodies, which contain high levels of the overexpressed protein. Such protein aggregates typically must be recovered, solubilized, denatured and refolded using techniques well known in the art (Kreuger et al., 1990; U.S. Pat. No. 4,923,967).

Preparation of GLP-1 Analogs and Derivatives

Alterations to a precursor GLP-1 or GLP-1 amino acid sequence to produce a desired GLP-1 analog or GLP-1 derivative, or active fragment thereof, are made by well-known methods: chemical modification, enzymatic modification, or a combination of chemical and enzymatic modifications. The techniques of classical solution phase methods and semi-synthetic methods may also be useful for preparing the GLP-1 molecules used in the present invention. Methods for preparing the GLP-1 molecules of the present invention are well known to an ordinarily skilled peptide chemist.

Addition of an acyl group to the epsilon amino group of Lys$^{34}$ may be accomplished using any one of a variety of methods known in the art (*Bioconjugate Chem*. 1990; Hashimoto et al., 1989).

For example, an N-hydroxy-succinimide ester of octanoic acid can be added to the lysyl-epsilon amine using 50% acetonitrile in borate buffer. The peptide can be acylated either before or after the imidazolic group is added. Moreover, if the peptide is prepared recombinantly, acylation prior to enzymatic cleavage is possible. Also, the lysine in the GLP-1 derivative can be acylated as taught in WO 96/29342.

The existence and preparation of a multitude of protected, unprotected, and partially-protected, natural and unnatural, functional analogs and derivatives of GLP-1 (7-36)amide and GLP-1 (7-37) molecules have been described (U.S. Pat. Nos. 5,120,712; 5,545,618 and 5,118,666; Orskov et al., 1989; WO 91/11457).

Optionally, the amino and carboxy terminal amino acid residues of GLP-1 derivatives may be protected, or, optionally, only one of the termini is protected. Reactions for the formation and removal of such protecting groups are described in works known to those of skill in the art including, for example, *Protective Groups in Organic Chemistry* 1973; Green, 1981; Schröder and Lübke, 1965. Representative amino-protecting groups include, for example, formyl, acetyl, isopropyl, butoxycarbonyl, fluorenyl-methoxycarbonyl, carbobenzyloxy, and the like. Representative carboxy-protecting groups include, for example, benzyl ester, methyl ester, ethyl ester, t-butyl ester, p-nitro phenyl ester, and the like.

Carboxy-terminal, lower-alkyl-ester, GLP-1 derivatives used in the present invention are prepared by reacting the desired ($C_1$–$C_4$) alkanol with the desired polypeptide in the presence of a catalytic acid such as hydrochloric acid. Appropriate conditions for such alkyl ester formation include a reaction temperature of about 50° C. and reaction time of about 1 hour to about 3 hours. Similarly, alkyl ester derivatives of the Asp and/or Glu residues can be formed.

Preparation of a carboxamide derivative of a compound used in the present invention is formed, for example, as described in Stewart et al., 1984.

A pharmaceutically-acceptable salt form of GLP-1, of a GLP-1 analog, or of a GLP-1 derivative may be used in the present invention. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. The salt forms are particularly preferred.

A GLP-1, GLP-1 analog, or GLP-1 derivative used in the present invention may be formulated with one or more excipients before use in the present invention. For example, the active compound used in the present invention may be complexed with a divalent metal cation by well-known methods. Such metal cations include, for example, $Zn^{++}$, $Mn^{++}$, $Fe^{++}$, $Co^{++}$, $Cd^{++}$, $Ni^{++}$, and the like.

Compositions of the Invention

Optionally, the active compound used in the present invention may be combined with a pharmaceutically-acceptable buffer, and the pH adjusted to provide acceptable stability, and a pH acceptable for parenteral administration.

Optionally, one or more pharmaceutically-acceptable anti-microbial agents may be added. Meta-cresol and phenol are preferred pharmaceutically-acceptable anti-microbial agents. One or more pharmaceutically-acceptable salts may be added to adjust the ionic strength or tonicity. One or more excipients may be added to further adjust the isotonicity of the formulation. Glycerin is an example of an isotonicity-adjusting excipient.

GLP-1 receptors and the signal transduction cascade initiated by ligand binding to the GLP-1 receptor are described in WO 96/25487; Thorens, 1992; Thorens et al., 1993; Widmann et al., 1994. The GLP-1 receptor is a membrane protein with seven transmembrane domains, coupled to heterotrimeric G-proteins that link activation of the receptor by ligand binding to production of intracellular secondary messengers, especially, cyclic adenosine monophosphate (cAMP). cAMP, in turn, activates a specific protein kinase, cAMP-dependent protein kinase (protein kinase A, PKA). This enzyme phosphorylates a number of key response elements present in the promoter region of certain genes. In pancreatic b-cells and other neuroendocrine cells, phosphorylation of some specific proteins of the regulated secretory pathway stimulates peptide secretion by stimulating exocytosis of secretory granules.

Various compounds are known to stimulate secretion of endogenous GLP-1. For example, exposure of STC-1 cells to certain secretagogues, such as, the adenylate cyclase activator, forskolin, or the protein kinase-C-stimulating agent, 12-O-tetradecanoylphorbol-13-acetate (TPA), caused significant increases in release of GLP-1 (Abello etal., 1994). The STC-1 cell line originated from an intestinal tumor in transgenic mice carrying insulin-promoting oncogenes, and STC-1 cells are known to contain m-RNA transcripts of pro-glucagon, from which GLP-1 is generated. Other compounds, such as, somatostatin, gastric inhibitory polypeptide, glucose-dependent insulinotropic peptide, bombesin, calcitonin gene-related peptide, gastrin-releasing peptide, cholinergic agonists, the b-adrenergic agonist, isoproterenol, and the muscarinic cholinergic agonist, bethanechol, are similarly known to cause release of endogenous GLP-1 (Plaisancie et al., 1994; Orskov et al., 1986; Brubaker, 1991; Buchan, et al., 1987).

Administration of Compositions

Administration may be via any route known to be effective by the physician of ordinary skill, except that parenteral administration directly into the central nervous system is not a route taught or claimed in this invention. Peripheral, parenteral administration is preferred. Parenteral administration is commonly understood in the medical literature as the injection of a dosage form into the body by a sterile syringe or some other mechanical device such as an infusion pump. For the purpose of this invention, peripheral parenteral routes include intravenous, intramuscular, subcutaneous, and intraperitoneal routes of administration. Intravenous, intramuscular, and subcutaneous routes of administration of the compounds used in the present invention are more preferred. Intravenous and subcutaneous routes of administration of the compounds used in the present invention are yet more highly preferred. For parenteral administration, an active compound used in the present invention preferably is combined with distilled water at an appropriate pH.

Certain compounds used in the present invention to effect weight-loss may also be amenable to administration by the oral, rectal, nasal, or lower respiratory routes, which are non-parenteral routes. Of the said non-parenteral routes, the lower respiratory route is preferred for administration of peptides used in the instant invention. Various formulations of peptide compounds for administration by the lower respiratory tract are disclosed in U.S. Pat. Nos. 5,284,656 and 5,364,838. Publication WO 96/19197 discloses aerosol formulations of various peptides suitable for enhancing lower respiratory tract absorption of the compounds used in the instant invention. The oral route of administration is preferred for compounds used in the instant invention.

Additional pharmaceutical methods may be employed to control the duration of action. Controlled release preparations may be achieved by the use of polymers to complex or absorb the active compound used in the present invention. Extended duration may be obtained by selecting appropriate macromolecules, for example, polyesters, polyamino acids, polyvinylpyrrolidone, ethylenevinyl acetate, methylcellulose, carboxymethylcellulose, or protamine sulfate, and by selecting the concentration of macromolecules, as well as the methods of incorporation, in order to prolong release. Another possible method to extend the duration of action by controlled release preparations is to incorporate an active compound used in the present invention into particles of a polymeric material such as polyesters, polyamino acids, hydrogels, poly (lactic acid) or ethylene vinylacetate copolymers. Alternatively, instead of incorporating a compound into these polymeric particles, it is possible to entrap a compound used in the present invention in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are known to those of skill in the art and disclosed, e.g. in *Remington's Pharmaceutical Sciences*, 1980.

Dose

The dose of GLP-1, GLP-1 analog, or GLP-1 derivatives, or active fragments effective in a particular subject to cause weight-loss will depend on a number of factors, among which are included the subject's sex, weight and age, the underlying causes of obesity, the route of administration and bioavailability, the persistence of the administered compound in the body, the formulation, and the potency. Where administration is intermittent, the dose per administration should also take into account the interval between doses, and the bioavailability of the administered compound. Where administration is continuous, a suitable dosage rate is between 0.25 and 6 pmol/kg body weight/min, preferably from about 0.5 to about 1.2 pmol/kg/min. It is within the skill of the ordinary physician to titrate the dose and rate of administration of compositions containing GLP-1, GLP-1 analogs, or GLP-1 derivatives, or active fragments thereof to achieve the desired clinical result, that is weight loss.

"Pharmaceutically acceptable" means suitable for administration to a human, that is, does not contain toxic elements, undesirable contaminants or the like, and does not interfere with the activity of the active compounds therein.

The present invention will be more readily understood by reference to a specific example, which is provided to illustrate, not to limit, the present invention.

EXAMPLE 1

Four patients having non-insulin dependent diabetes mellitus (NIDDM) (3 male, 1 female; age: 60.2±1,8 years; starting BMI: 33.5±1.4 kg/m$^2$; starting body weight: 97.5±6.5 kg; starting waist/hip: 0.946±0.036; starting HbA$_{1c}$: 7.1±0.3%; fasting blood glucose: 7.2±1.1 mM) received continuous, subcutaneous infusions of GLP-1(7-36) amide for four weeks. Solutions of GLP-1 were prepared by combining 100 nmol of GLP-1(7-36) amide and 0.025 mL human albumin solution (20%), then adjusting the pH to 4 using 5 molar acetic acid, and finally bringing the volume to 1 mL using normal saline. The solution was administered at a GLP-1 dose rate of 1.2 pmol/kg/minute. The volumetric delivery rate of the Minimed pump (Minimed Europe, Paris) used to administer the GLP-1 solution was 0.05–0.07 mL/h. The subcutaneous site of administration was the abdomen.

This treatment with GLP-1 was compared with two weeks of intensive insulin therapy prior to and after the GLP-1 infusion. During the insulin treatment periods, insulin was administered subcutaneously before each meal (see Table 1). During the GLP-1 infusion, no insulin was administered. During both the insulin treatment periods, and the GLP-1 treatment period, the patients adhered to a standard diabetic diet consisting of, on a caloric basis, about 55% carbohydrate, 30% fat, and 15% protein. No exercise regimen was followed. The patients were not hospitalized, and remained out-patients throughout the entire trial period.

During GLP-1 treatment, the four patients lost an average of 3.5±1.2 kg body weight, while they lost only 1.3±0.6 kg during the first two weeks of intensive insulin treatment, and actually gained weight, on average, during the second two weeks of intensive insulin treatment. All values are individual values, or mean±SEM (standard error of the mean). No data are available for patient MP for the second insulin treatment period.

TABLE 1

Insulin Treatment Regimes. The four values represent the amount of insulin administered subcutaneously (IU) to each patient just prior to four daily meals. The first insulin treatment preceded, and the second insulin treatment followed 4 weeks of GLP-1 treatment

| Patient | First Insulin Treatment (2 weeks) | Second Insulin Treatment (2 weeks) |
|---|---|---|
| VN | 47; 39; 35; 53 | 21; 20; 28; 26 |
| NW | 12; 13; 11; 12 | 11; 10; 12; 12 |
| HF | 11; 10; 12; 56 | 11; 10; 12; 12 |
| MP | 20; 14; 34; 30 | — |

TABLE 2

Patient Weight and Weight Change. GLP-1 (7-36) amide was administered by continuous subcutaneous infusion for four weeks, immediately preceded and followed by two weeks of intensive insulin therapy.

| Patient | Initial | Patient Weight (kg) | | | Weight Change (kg) | | |
|---|---|---|---|---|---|---|---|
| | | First Insulin 2 weeks | GLP-1 4 weeks | Second Insulin 2 weeks | First Insulin 2 weeks | GLP-1 4 weeks | Second Insulin 2 weeks |
| VN | 101.5 | 99.0 | 92.0 | 95.0 | −2.5 | −7.0 | 3.0 |
| NW | 113.0 | 111.0 | 108.0 | 108.0 | −2.0 | −3.0 | 0.0 |
| HF | 94.0 | 93.5 | 91.5 | 91.5 | −0.5 | −2.0 | 0.0 |
| MP | 82.0 | 81.9 | 80.0 | — | −0.1 | −1.9 | — |
| | 97.5 ± 6.5 | 96.4 ± 6.0 | 92.9 ± 5.8 | 98.2 ± 5.0 | −1.3 ± 0.6 | −3.5 ± 1.2 | +1.0 ± 1.0 |

Documents Cited

The documents cited below provide information useful for practice of the invention; the U.S. Patents are incorporated by reference in the U.S.

Abello, J., et al., *Endocrinol.* 134:2011–2017 (1994)
American Diabetes Association, Detection and Management of Lipid Disorders in Diabetes, Consensus Statement, *Diabetes Care* 18:86–93 (1995)
American Diabetes Association, Standards of Medical Care for Patients with Diabetes Mellitus, Consensus Statement, *Diabetes Care* 18:8–15 (1995)
Billock, B. P., et al., *Endocrinology* 137:2968–2978 (1996)
*Bioconjugate Chem.* "Chemical Modifications of Proteins: History and Applications" pages 1, 2–12 (1990)
Brown, et al. *Methods in Enzymology*, Academic Press, N.Y., 68:109–151 (1979)
Brubaker, P. L. *Endocrinol.* 128:3175–3182 (1991)
Buchan, A. M. J., et al., *Gastroenterol.* 93:791–800 (1987)
Dugas, H. and Penney, C., *Bioorganic Chemistry*, Springer-Verlag, New York, pp. 54–92 (1981)
Fehmann, H.-C., et al., *Endocrinology* 130:159–166 (1992)
Fehmann, H.-C., et al., *Endocr. Rev.* 16:390–410 (1995)
Green, T. H., "Protective Groups in Organic Synthesis", Wiley, New York (1981)
Gutniak M., et al., *New England J. Med.* 326:1316–1322 (1992)
Hashimoto et al., *Pharmaceutical Res.* 6(2):171–176 (1989)
Kanse, S. M., et al., *FEBS Lett.* 241 209–212 (1988)
Krcymann B., et al., *Lancet* 2:1300–1303 (1987)
Krcymann, B., et al., *Brain Research* 502:325–331 (1989)
Kreuger, et al. in *Protein Folding*, Gierasch and King, eds., pgs 136–142, American Association for the Advancement of Science Publication No. 89–18S, Washington, D.C. (1990)
Lund, et al., *Proc. Natl. Acad. Sci. U.S.A.* 79:345–349 (1982)
Maniatis et al. *Molecular Cloning; A Laboratory Manual*, Cold Springs Harbor Laboratory Press, N.Y., Vol. 1–3 (1989)
Mentlein, R., et al., *Eur. J. Biochem.*, 214:829–835 (1993)
Merrifield, J. M., *Chem. Soc.*, 85:2149 (1962)
Mojsov, S., et al., *J. Biol. Chem.* 261:11880–11889 (1986)
Mojsov, S., *Int. J. Peptide Protein Research*, 40:333–343 (1992)
Morley, J. E., *Endocr. Rev.* 8:256–287 (1987)
Nauck, M. A. et al., *J. Clin. Invest.* 91:301–307 (1993)
Nilsson, O., et al., *Endocrinol.* 129:139–148 (1991)
Oben, J. et al., *J Endocrinol.* 130:267–272 (1991)
Orskov, C., et al., *Endocrinol.* 119:1467–1475 (1986)
Orskov, C., et al., *J. Biol. Chem.* 264(22):12826–12829 (1989)
Orskov, C., et al., *Diabetologia* 38 (Suppl. 1, Abstract):A39 (1995)
Orskov, C., et al. *Diabetes* 45:832–835 (1996)
O'Shea, et al., *NeuroReport* 7:830–832 (1996)
Plaisancie, P., et al., *Endocrinol.* 135:2398–2403 (1994)
*The Promega Biological Research Products Catalogue* Promega Corp., 2800 Woods Hollow Road, Madison, Wis., 53711-5399 (1992)
*Protective Groups in Organic Chemistry*, Plenum Press, London and New York (1973)
*Remington's Pharmaceutical Sciences* (1980)
Rowland, N. E., et al., *Nutrition* 12:626–639 (1996)
Ruiz-Grande, C., et al., *Peptides* 13:13–16 (1992)
Schröder and Lüke, "The Peptides", Vol. I, Academic Press London and New York (1965)
Stewart and Young, *Solid Phase Peptide Synthesis*, Freeman, San Francisco pp. 24–66 (1969)
Stewart, J. M., et al., *Solid Phase Peptide Synthesis*, Pierce Chemical Company Press, (1984)
*The Stratagene Cloning Systems Catalogue* Stratagene Corp., 11011 North Torrey Pines Road, La Jolla, Calif., 92037 (1992)
Suzuki, S., et al. *Endocrinol.* 125:3109–3114 (1989)
Thorens, B., *Proc. Natl. Acad. Sci. USA* 89:8641–8645 (1992)
Thorens, B., et al., *Diabetes* 42:1678–1682 (1993)
Turton, M. D., et al., *Nature* 379:69–72 (1996)
U.S. Pat. No. 4,710,473
U.S. Pat. No. 4,923,967
U.S. Pat. No. 5,118,666
U.S. Pat. No. 5,120,712
U.S. Pat. No. 5,284,656
U.S. Pat. No. 5,364,838
U.S. Pat. No. 5,512,549
U.S. Pat. No. 5,523,549
U.S. Pat. No. 5,545,618
Valverde, I., et al. *Endocrinology* 132:75–79 (1993)
Villanueva, M. L., et al., *Diabetologia* 37:1163–1166 (1994)
Widmann, C., et al., *Mol. Pharmacol.* 45:1029–1035 (1994)

WO 91/11457 (Buckley, D. I., et al., published Aug. 8, 1991)
WO 96/19197
WO 96/25487 (Thorens, B. et al., published Aug. 22, 1996)
WO 96/29342
WO 97/31943 (Thim, 1. et al., published Sep. 4, 1997)

We claim:

1. A method of reducing body weight in a subject in need of body weight reduction by administering to the subject a composition comprising an agonist of the GLP-1 receptor wherein the agonist is a GLP-1 analog which comprises the substitution of D-Serine, D-Cysteine, Sar, D-Alanine, beta-Alanine, or Aib for Alanine at position 8 of GLP-1 in a dose sufficient to cause reduction in body weight for a period of time effective to produce weight loss.

2. The method of claim 1 wherein the composition further comprises a pharmaceutically acceptable buffer.

3. The method of claim 2 wherein the composition further comprises an anti-microbial agent.

4. The method of claim 3 wherein the anti-microbial agent is selected from phenol and meta-cresol.

5. The method of claim 3 further comprising an isotonicity agent.

6. The method of claim 1 wherein the composition is administered by a non-parenteral route selected from the group consisting of: oral, rectal, nasal, and lower respiratory.

7. The method of claim 1 wherein the composition is a controlled release preparation.

8. The method of claim 7 wherein the controlled release preparation comprises particles of a polymeric material.

* * * * *